United States Patent [19]

Schultz

[11] Patent Number: 4,699,789

[45] Date of Patent: Oct. 13, 1987

[54] VIRAL FREE SEMEN AND METHODS OF PRODUCING THE SAME

[75] Inventor: Ronald D. Schultz, Verona, Wis.

[73] Assignee: Eastern Artificial Insemination Cooperative, Inc., Ithaca, N.Y.

[21] Appl. No.: 781,137

[22] Filed: Sep. 27, 1985

[51] Int. Cl.$^4$ .............................................. A61K 35/52
[52] U.S. Cl. ......................................... 424/105; 435/2
[58] Field of Search ............................ 435/2; 424/105

[56] References Cited

U.S. PATENT DOCUMENTS

| | | |
|---|---|---|
| 3,472,735 | 10/1969 | Nishikawa et al. . |
| 3,687,806 | 8/1972 | van den Bovenkamp . |
| 3,718,740 | 2/1973 | Hafs et al. . |
| 3,816,249 | 6/1974 | Bhattacharya . |
| 3,973,003 | 8/1976 | Colas . |
| 4,009,260 | 2/1977 | Ericsson .................................. 435/2 |
| 4,085,205 | 4/1978 | Hancock ............................. 424/105 |
| 4,191,749 | 3/1980 | Bryant . |
| 4,329,337 | 5/1982 | Sexton . |
| 4,448,767 | 5/1984 | Bryant ................................. 424/105 |

OTHER PUBLICATIONS

R. D. Breckon, A. J. Luedke, T. E. Walton, "Bluetongue Virus in Bovine Semen: Viral Isolation", Am J Vet Res, vol. 41, No. 3, pp. 439–442, Mar. 1980.

J. Branny & M. Zembala, "Some Characteristics of Viruses Isolated From B Ull Semen and Their Possible Pathogenicity", Branny & Zembala, Br. vet. F., (1971), 127,2.

*Primary Examiner*—Sam Rosen
*Attorney, Agent, or Firm*—Cushman, Darby & Cushman

[57] ABSTRACT

The elimination or reduction of viral contamination of semen used for artificial insemination by incorporating with the semen a diluent or extender containing antibodies for the particular virus or viruses. These extenders containing the antibodies can be serum, milk, egg yolk, culture supernatant or ascites fluid with bovine monoclonal antibodies or gamma globulin fractions of each of the above.

18 Claims, No Drawings

VIRAL FREE SEMEN AND METHODS OF PRODUCING THE SAME

BACKGROUND OF THE INVENTION

1. Field of the Invention

The present invention generally relates to the production of semen for artificial insemination in animals. More specifically, the present invention is concerned with a process which will eliminate or reduce infectious virus contamination in semen and semen free of infectious virus thereby produced.

2. Description of the Prior Art

In the artificial insemination of animals, it is well-known that the semen can potentially be contaminated with different viruses that can cause a variety of diseases. At present, there is no safe or effective procedure to eliminate viral contamination from semen even though it is known that bacterial contamination of semen can be eliminated or reduced by the addition of antibiotics. No drug presently available will similarly eliminate virus without significantly affecting the viability of the sperm. (See, e.g. Bartlett et al, "Specific Pathogen Free (SPF) Frozen Bovine Semen: A Goal?", Proc. 6th Tech. Conf. on AI and Repro. N.A.A.B., pp. 11–12 (1976); and Schultz, "When Can We Achieve Our Goal of Providing Specific Pathogen Free Bovine Semen?" U.S.A.H.A. Proc., 81:141–140 (1979)). It has also been suggested that when antibody is present as a result of immunization or previous infection in body fluids or when this antibody, if present in serum, milk or egg yolks, is added to viruses in vitro rapidly eliminates or reduces their infectivity for susceptible cells in culture or eliminates infectivity for susceptible animals. (See, Bellanti, Immunology II, W. B. Saunders Co., Philadelphia, PA. (1978). Myrvik and Weisen, Fundamentals of Immunology, Lea & Febiger, Philadelphia, PA (1984)).

Viral contamination of semen has serious implications for the cattle industry since one infected bull shedding virus in his semen could potentially infect cattle regionally, nationally or even internationally thereby leading to quarantine and/or destruction of valuable livestock as a result of infection and/or disease. Artificial insemination and the procedures used for the performance of artificial insemination serve as a means by which viral contaminated semen could be collected, preserved, stored and disseminated to the cattle population without the knowledge of the parties involved.

It is apparent that because of the potential danger that viral contaminated semen presents to the cattle industry, there is a distinct need for a method which will eliminate or reduce viral contamination of semen thus eliminating the problem for both the artificial insemination industry and the cattle producer. Although the need has been apparent, this need went unanswered until the present invention.

It has been proposed in the art that semen can be preserved for a period of time as evidenced by U.S. Pat. Nos. 3,472,735 and 4,329,337. However, as the reader will appreciate from an inspection of those U.S. patents, no solution to the elimination of viral contaminated semen has been suggested. Thus although such proposals may permit storage of semen, the semen which is stored may be contaminated with various viruses. (e.g., Bartlett et al, "Specific Pathogen (SPF) Frozen Bovine Semen: A Goal?", Proc. 6th Tech. Conf. on AI and Repro. N.A.A.B., pp. 11–12 (1976).

BRIEF SUMMARY OF THE INVENTION

According to the present invention, however, a process is provided for eliminating or reducing viral infectivity in contaminated semen.

In accordance with the present invention, it has been found that if semen is extended or diluted with serum, milk or egg yolk containing sufficient antibodies specific for contaminating viruses present in the semen, the viruses would be rendered incapable of infecting cattle when used in artificial insemination procedures. This extender containing the antibodies, hereinafter referred to by the terminology "immunoextendor", can conceivably be developed for any virus that would contaminate semen. If desired, the "immunoextendor" can contain antibodies specific for numerous viruses without, once again, affecting the semen viability.

The novel semen product of the present invention is particularly well suited for use in artificial insemination. The semen of the present invention achieves such beneficial results when it contains an "immunoextendor", the "immunoextendor" containing antibodies which will effectively eliminate or reduce viral contamination without impeding the viability of fertility of the supernatant or ascites fluid containing bovine monoclonal antibody, or gamma globulin fractions of any or all of the above.

Therefore, in accordance with the present invention, a process is provided which produces semen of the highest quality, free of infectious viruses and with a high conception rate.

These and other objects and advantages of the present invention will become more apparent to the reader after careful consideration is given to the following detailed description of the preferred exemplary embodiments thereof.

DETAILED DESCRIPTION OF THE PREFERRED EXEMPLARY EMBODIMENTS

It has been found that viral contamination of semen can be eliminated or substantially reduced by antibodies without interfering with the viability of the semen. Semen for use in artificial insemination is usually diluted or extended with various diluents to obtain the most economical use thereof. In accordance with the present invention, antibodies specific for various viruses may then be incorporated into the extender. As used herein and in the accompaning claims, the term "immunoextendor" is meant to refer to a semen extender having viral antibodies incorporated therein.

The addition of the "immunoextendor" to semen intentionally contaminated with large amounts of viruses (Infectious Bovine Rhinotracheitis (IBR), Bovine Virus Diarrhea (BVD) and Bluetongue (BT) viruses) eliminates infectious virus as determined by inoculating susceptible cell cultures and animals, but does not interfere with sperm viability as determined by sperm motility and ability of the sperm to cause conception after artificial insemination. The "immunoextendors" of the present invention include "immunoextendor"-hyperimmune serum, "immunoextendor"-milk, "immunoextendor"-egg yolk, "immunmoextendor"-monoclonal antibody, "immunoextendor"-gamma-globulin. These "immunoextendors" when used in the process of extending semen for artificial in insemination in accordance with this invention have been found to reduce or eliminate viral contamination of the semen, rendering it noninfectious when used to inseminate cattle. Importantly, the "immunoextendor" does not interfere with the ability of the sperm to cause conception. The advantage of using the immunoextendor and the procedure of immunoextension is to provide a semen which is free of infectious virus thus providing a more desirable product for artificial insemination.

Hyperimmune serum, hyperimmune milk, hyperimmune egg yolk, gamma globulin from hyperimmune serum or milk, bovine monoclonal antibodies ("Immunoextendor") can be developed for any virus known to contaminate semen. The "immunoextendor" may, when desirable, contain antibody activity to several viruses (e.g., IBR, BVD, BT, foot and mouth disease (FMD) viruses). "Immunoextendors" with multiple reactivity would have broad spectrum coverage to eliminate any one or more viruses that may contaminate a specific semen sample. It is proposed that "immunoextendor" be considered similar to antibiotics which are currently used by the artificial insemination industry to eliminate or reduce bacterial contamination of semen.

The "immunoextendor" of the present invention is five distinct, but similar in purpose, products. (1) The first "immunoextendor" is hyperimmune serum (high antibody titer to the virus or viruses one wishes to eliminate) that is added to the extender (milk or egg yolk) and the semen. The hyperimmune serum can be added to standard milk or to egg yolk extenders to convert them to an "immunoextendor." (2) The second "immunoextendor" is hyperimmune milk, produced by systemic and/or intramammary immunization of non-lacting cows. The immune milk which is collected shortly after parturition is used as an "immunoextendor" for semen or can be added to standard milk or to egg yolk extender. (3) The third "immunoextendor" is hyperimmune egg yolk. Laying chickens are immunized with the desired virus and eggs are collected on a daily basis after high titers of serum antibody are present. The egg yolk is collected, pooled and an isotonic buffered egg yolk citrate preparation is prepared as the "immunoextendor." (4) The fourth "immunoextendor" is a bovine monoclonal antibody the product of a hybridoma cell producing antibody to the neutralizing antigen of the virus. Mouse monoclonal antibodies are undesirable, because of their inherent antigenicity in the bovine species. (5) The fifth "immunoextendor" is the gamma globulin fraction of all of the above (described in 1 to 4) prepared by ammonium sulfate or alcohol precipitation of the same to provide a partially purified concentrate of the gamma globulin faction which contains the antibodies.

Studies which have included the "immunoextendors" described above have demonstrated that semen experimentally contaminated with large amount of virus (e.g., IBR, BVD or BT viruses) and extended with "immunoextendor" are free of infectious virus when the semen is placed in tissue culture or used to inoculate and/or inseminate virus susceptible animals. Furthermore, the "immunoextendors" do not interfere with conception and the fertility of semen extended with "immunoextendors" is equal to or better than non-immunoextendor-treated semen.

The following non-limiting examples will further illustrate and describe the "immunoextendors" of the present invention and their preparation.

EXAMPLE I

Hyperimmune Serum

Holstein and Holstein-Angus cross, virgin heifers approximately 1 to 2 years old were used to produce hyperimmune serum to IBR, BVD and BT viruses. Commercial intramuscular IBR and BVD vaccine and a laboratory attenuated BT-serotype 17 virus were used for the antigens. A multiple intramuscular (3 times) followed by intranasal immunization (1 time) was used to stimulate a high antibody titer. Three months after the last immunization, the heifers were treated with 10 mg of dexamethasone (Azium)/day for 5 days, then reimmunized on the fifth day with BVD and BT viruses. Serum was collected on the 7th and 14th day after the BVD and BT viruses were inoculated. The antibody titers were determined by the serum neutralization test (constant virus as well as constant serum).

The antibody titer for IBR was greater than 1:1000, for BVD greater than 1:2,500 and for BTV greater than 1:500. The serum was heat treated at 60° C. for 2 hours. This procedure would effectively destroy infectious virus, inactivate certain of the complement components and destroy immunoglobulin E activity, all are unwanted and unneeded components of the serum. The serum was tested in aerobic and anaerobic culture conditions for bacterial contamination. The serum was placed on bovine turbinate cell culture and blind passaged three times to ensure that no cytopathic virus was present. Hyperimmune serum to be used commercially could be subjected to ionizing radiation to ensure that virus, if present, would be destroyed.

EXAMPLE II

Hyperimmune Milk

Two Holstein cows in the 6th month of gestation were immunized intramuscularly and intramammary via the teat canal with IBR and BVD. The animals were immunized again at the 8th month in a similar manner. At parturition, the colostrum and the next six milkings were pooled, placed in plastic containers and frozen. A small aliquot of the total milk sample was tested for antibody as described above for serum. The antibody titer to IBR was greater than 1:400 and greater than 1:1000 for BVD virus. The milk was heated to 60° C. for 1 hour and tested for sterility as described above for hyperimmune semen.

EXAMPLE III

Hyperimmune Egg Yolk

Eight White Leghorn laying hens were used. Two were hyperimmunized with IBR, two hyperimmunized with BVD and four hyperimmunized with IBR and BVD. Immunization included subcutaneous and intramuscular inoculation during a one month period. Eggs were collected daily and the yolks were separated from the whites, pooled and tested for antibody.

Antibody titer to IBR was approximately 1:100 and for BVD virus was approximately 1:500. The egg yolk was prepared as an egg yolk citrate extender.

EXAMPLE IV

Monoclonal Antibodies

Bovine x mouse hybridoma would be prepared as previously described (Srikumaran, Guidry and Goldsby. "Bovine X Mouse Hybridomas that Secrete Bovine IgG$_1$", Science, Vol. 220, pp. 522–524, 1983, expressly incorporated hereinto by reference). The monoclonal antibody was screened for neutralizing activity to IBR virus. The monoclonal antibody was added to milk or egg yolk extender to produce "immunoextendor".

EXAMPLE V

Gamma Globulin Fraction

Hyperimmune serum, milk, egg yolk and monoclonal antibody was precipated with ammonium sulfate or ethanol according to standard procedures to obtain a crude gamma globulin fraction. The gamma globulin fractions are superior to all the above preparations because the concentration of antibodies can be increased, they do not contain unwanted protein fractions (e.g., albumin), small mounts can be added, and the ethanol would sterilize the preparation, eliminating possible microbial contaminants.

Immunoextension

Semen was collected from Holstein and Jersey bulls by standard methods.

Part of the semen from the Holstein bulls and/or the Jersey bulls was contaminated with various concentrations of IBR and BVD viruses or BT virus. One-half of the contaminated semen was diluted in extender containing hyperimmune serum so that the final diluted semen had 20% serum.

Contaminated semen was also diluted in hyperimmune milk (50%), hyperimmune egg yolk (100%), monoclonal antibody and gamma globulin fractions of hyperimmune serum. The gamma globulin fractions would be equivalent in antibody titer to adding 20%, 50% or 80% whole hyperimmune serum. The remaining contaminated semen was diluted and frozen in normal extender, (milk or egg yolk citrate with nonimmune serum, or gamma globulin from a non-immune animal).

Semen Examination

Semen was tested by standard method for numbers and motility.

The ability of the semen extended with hyperimmune serum and gamma globulin fraction "immunoextendors" to settle cows was tested in experimental as well as large field trials by standard methods of artificial insemination.

Results

Results of in vitro and in vivo tests to detect virus in contaminated semen are listed in Table 1. Semen contaminated with IBR and BVD extended with hyperimmune serum and hyperimmune milk did not have infectious virus which could be detected by either in vitro or in vivo tests when concentrations as high as $1 \times 10^4$ TCID$_{50}$ IBR and BVD virus were added to semen. The gamma globulin fraction of hyperimmune serum eliminated virus from the semen containing $1 \times 10^6$ TCID$_{50}$ of IBR and BVD. The "immunoextendor" was also effective in reducing or eliminating infectious bluetongue virus in semen (Table 2).

Sperm motility was good after addition of "immunoextendor". The sperm extended with hyperimmune serum when used for insemination was able to "settle" (cause conception) heifers (Table 3). These results clearly demonstrate that immunoextension with hyperimmune serum or a gamma globulin fraction thereof and hyperimmune milk are effective in reducing or eliminating virus from semen and that the semen is able to cause conception. The inability of the egg yolk in this trial to similarly reduce or eliminate virus was caused by the low neutralization titer of the egg yolk used but nonetheless the results suggest this method could also be used if egg yolk with higher titer antibody to virus was used. Results with monoclonal antibodies suggest they are equal to or better than hyperimmune serum.

TABLE 1.

Results of Viral Infectivity for Semen Contaminated with Infectious Bovine Rhinotracheitis Virus and Bovine Virus Diarrhea and Extended with Normal Extender or "Immunoextendor".

| | EXTENDER | | | | | | | | | | | | |
|---|---|---|---|---|---|---|---|---|---|---|---|---|---|
| | Serum | | | | | Milk | | | | | Egg Yolk | | | |
| | Normal | | Hyperimmune ("Immunoextendor") | | Gamma Globulin | Normal | | Hyperimmune ("Immunoextendor") | | Gamma Globulin | Normal | | Hyperimmune ("Immunoextendor") | |
| Concentration of Virus (IBR & BVD) | In Vitro[a] | In Vivo[b] | In Vitro | In Vivo | In Vivo | In Vitro | In Vivo | In Vitro | In Vivo | In Vivo | In Vitro | In Vivo | In Vitro | In Vivo |
| $1 \times 10^3$ | Pos[c] | Pos | Neg[d] | Neg | Neg | Pos | Pos | Neg | Neg | Neg | Pos | Pos | Neg | Pos |
| $1 \times 10^4$ | Pos | Pos | Neg | Neg | Neg | Pos | Pos | Neg | Neg | Neg | Pos | Pos | Pos | Pos |
| $1 \times 10^6$ | Pos | Pos | Neg | Pos | Neg | Pos | Pos | Pos | Pos | Pos | Pos | Pos | Pos | Pos |

[a] tissue
[b] animal inoculation
[c] virus isolated or seroconversion
[d] no virus isolated or animals did not seroconvert

TABLE 2

Results of Viral Infectivity for Semen Contaminated with Bluetongue Virus (Serotype 17) Extended with Normal Extender or "Immunoextendor".

| | EXTENDER Serum | | |
|---|---|---|---|
| Concentration of Virus (TCID50) | Normal In Vivo[a] | Hyperimmune In Vivo | Gamma Globulin Fraction In Vivo |
| $1 \times 10^2$ | Pos[b] | Neg | Neg |
| $1 \times 10^3$ | Pos | Neg | Neg |
| $1 \times 10^4$ | Pos | Neg | Neg |
| $1 \times 10^5$ | Pos | Pos | Neg |
| $1 \times 10^6$ | Pos | Pos | Pos |

[a] Inoculation of susceptible cattle
[b] Seroconversion Pos. indicates animal became infected. Neg. indicates no infection

TABLE 3

Effect of Use of "Immunoextendor" (10% Hyperimmune Serum and Gamma Globulin) on Conception.

| Semen | Treatment | % Pregnant 1st Service |
|---|---|---|
| | Hyperimmune Serum (10%) | |
| Bull #1 | None | 44% |
| Bull #1 | Immunoextendor | 50% |

TABLE 3-continued

Effect of Use of "Immunoextendor" (10% Hyperimmune Serum and Gamma Globulin) on Conception.

| Semen | Treatment | % Pregnant 1st Service |
|---|---|---|
| Bull #2 | None | 56% |
| Bull #2 | Immunoextendor | 56% |
| Gamma Globulin Fraction (30% Equivalent) | | |
| Bull #3 | None | 75% |
| Bull #3 | Immunoextendor | 80% |
| Bull #4 | None | 64% |
| Bull #4 | Immunoextendor | 72% |
| Bull #5 | None | 76% |
| Bull #5 | Immunoextendor | 75% |
| Bull #6 | None | 66% |
| Bull #6 | Immunoextendor | 66% |

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the scope of the claims or that form their functional as well as conjointly cooperative equivalents are, therefore, intended to be embraced by those claims.

What is claimed is:

1. A non-infectious semen product for artificial insemination containing semen and viral antibodies said antibodies being of a type and being presenting an amount sufficient to reduce or eliminate viruses in the semen product while maintaining the viability of the semen.

2. The semen product of claim 1 wherein the viral antibodies are contained in a serum which is added to a milk or egg yolk citrate that dilutes the semen.

3. The semen product of claim 1 wherein the viral antibodies are contained in milk which dilutes the semen.

4. The semen product of claim 1 wherein the viral antibodies are contained in egg yolk which dilutes the semen.

5. The semen product of claim 1 wherein the viral antibodies are contained in a culture supernatant or ascites fluid, as bovine monoclonal antibodies, which is added to the milk or egg yolk citrate that dilutes the semen.

6. The semen product of any one of claims 2-5 wherein the viral antibodies are contained in a gamma globulin fraction.

7. The semen product of claim 6 wherein said gamma globulin fraction is prepared by ammonium sulfate or ethanol precipitation of the serum, milk, egg yolk, culture supernatant or ascites fluid.

8. The semen product of claim 1 wherein the viral antibodies neutralize one or more bovine viruses selected from the group consisting of Infectious Bovine Rhinotracheitis, Bovine Diarrhea Virus, Bluetongue Virus and Foot and Mouth Disease Virus.

9. A method for reducing or eliminating viral contamination in semen used for artificial insemination comprising incorporating viral antibodies in said semen to form a non-infectious semen product, said antibodies being of a type and being present in an amount sufficient to reduce or eliminate viruses in said semen while maintaining viability of the semen.

10. The method of claim 9 wherein the viral antibodies are contained in a serum which dilutes the semen.

11. The method of claim 9 wherein the viral antibodies are contained in milk which dilutes the semen.

12. The method of claim 9 wherein the viral antibodies are contained in egg yolk which dilutes the semen.

13. The method of claim 9 wherein the viral antibodies are contained in culture supernatant or ascites fluid, as bovine monoclonal antibodies, which dilute the semen.

14. The method of any one of claims 10-13 wherein the viral antibodies are contained in a gamma globulin fraction.

15. The method of claim 14 wherein the gamma globulin fraction is prepared by ammonium sulfate or ethanol precipitation of the serum, milk, egg yolk, culture supernatant or ascites fluid.

16. The method of claim 9 wherein the viral antibodies neutralize at least selected one virus from one group of bovine viruses consisting of Infectious Bovine Rhinotracheitis, Bovine Diarrhea Virus, Bluetongue Virus and Foot and Mouth Disease Virus.

17. The semen product of claim 1, wherein said semen is bovine semen.

18. The method of claim 9 wherein the semen is bovine semen.

* * * * *